(12) United States Patent
Miyoshi et al.

(10) Patent No.: US 7,402,435 B2
(45) Date of Patent: Jul. 22, 2008

(54) METHOD OF TRANSFERRING A SELECTED MOLECULE INTO A CELL

(75) Inventors: Sousuke Miyoshi, Osaka (JP); Akiko Ohkubo, Osaka (JP); Noriyuki Morikawa, Osaka (JP); Yasuhiro Ogawa, Osaka (JP); Shintaro Nishimura, Osaka (JP); Masao Fukagawa, Osaka (JP); Hiroyuki Arakawa, Osaka (JP); Jyunko Zenkou, Tsukuba (JP); Susumu Sato, Osaka (JP)

(73) Assignees: BBK Bio Corporation, Tokyo (JP); Pearl Kogyo Co., Ltd., Osaka-shi (JP)

( * ) Notice: Subject to any disclaimer, the term of this patent is extended or adjusted under 35 U.S.C. 154(b) by 457 days.

(21) Appl. No.: 10/470,732

(22) PCT Filed: Feb. 8, 2002

(86) PCT No.: PCT/JP02/01062

§ 371 (c)(1),
(2), (4) Date: Feb. 2, 2004

(87) PCT Pub. No.: WO02/064767

PCT Pub. Date: Aug. 22, 2002

(65) Prior Publication Data

US 2004/0110297 A1 Jun. 10, 2004

(30) Foreign Application Priority Data

Feb. 9, 2001 (JP) ................................ 200133176

(51) Int. Cl.
*C12N 15/00* (2006.01)
*C12N 15/02* (2006.01)

(52) U.S. Cl. ........................................ 435/455; 435/459
(58) Field of Classification Search ........................ None
See application file for complete search history.

(56) References Cited

U.S. PATENT DOCUMENTS 5,204,253 A * 4/1993 Sanford et al. .............. 435/459
6,099,523 A * 8/2000 Kim et al. ..................... 606/40

FOREIGN PATENT DOCUMENTS

JP 6-303963 11/1994
WO 91/18991 12/1991
WO 94/21117 9/1994

OTHER PUBLICATIONS

Ogawa et al. Biotechnology and Bioengineering, vol. 92, No. 7, Dec. 30, 2005, p. 865-870.*
Sakai et al. Journal of Biotechnology vol. 121, 2006, p. 299-308.*
Peters, http://www.accessexcellence.org/RC/AB/BA/Transforming_Plants.html, 1999, p. 1-3.*
R. S. Williams, et al., Proceedings of the National Academy of Sciences of the USA, vol. 88, No. 7, XP-000368688, pp. 2726-2730, "Introduction of Foreign Genes into Tissues of Living Mice by DNA-Coated Microprojectiles", Apr. 1, 1991.
Y. Maeda, et al., International Journal of Food Science and Technology, vol. 38, No. 8, XP-002269499, pp. 889-892, "Bactercidal Effect of Atmospheric Gas Plasma on *Escherichia coli* K12", Dec. 2003.
F. R. Pu, et al., Biomaterials, vol. 23, No. 24, XP-002269500, pp. 4705-4718, "Expression of Leukocyte-Endothelial Cell Adhesion Molecules on Monocyte Adhesion to Human Endothelial Cells on Plasma Treated Pet and PTFE in Vitro", Dec. 2002.
F. R. Pu, et al., Biomaterials, vol. 23, No. 11, XP-002269501, pp. 2411-2428, "Effects of Plasma Treated Pet and PTFE on Expression of Adhesion Molecules by Human Endothelial Cells in Vitro", Jun. 2002.
A. J. Kuijpers, et al., Journal of Biomedical Materials Research, vol. 51, No. 1, XP-002269502, pp. 136-145, "In Vivo Compatibility and Degradation of Crosslinked Gelatin Gels Incorporated in Knitted Dacron", Jul. 2000.
A. A. Deschamps, et al., Journal of Controlled Release, vol. 78, No. 1-3, XP-002269503, pp. 175-186, "Design of Segmented Poly(Ether Ester) Materials and Structures for the Tissue Engineering of Bone", Jan. 17, 2002.

* cited by examiner

*Primary Examiner*—L Blaine Lankford
*Assistant Examiner*—Laura Schuberg
(74) *Attorney, Agent, or Firm*—Oblon, Spivak, McClelland, Maier & Neustadt, P.C.

(57) ABSTRACT

A method of highly efficiently transferring various selected molecules into various cells and a method of fusing cells. Cells and/or selected molecules such as polynucleotide are treated with cold gas plasma to thereby transfer the selected molecules located around cells into the cells, or cells are fused by treating the cells with cold gas plasma. Moreover, an apparatus for transferring selected molecules or fusing cells having a cold gas plasma generation unit for transferring selected molecules into cells is provided.

11 Claims, 5 Drawing Sheets

Gas type: Air, Frequency: 23kHz, Pulse period: 60Hz, Duty: 50%

METHOD OF TRANSFERRING A SELECTED MOLECULE INTO A CELL

TECHNICAL FIELD

The present invention relates to a method of transferring a selected molecule, for example, polynucleotides such as genes, proteins, physiologically-active molecules and others into cells, and a method of fusing cells, or to an apparatus for these.

BACKGROUND ART

In genetic engineering and development of medicines in the field of recent medical science, pharmaceutics and others, there is increasing the necessity of transferring a selected molecule, for example, polynucleotides such as genes, proteins, physiologically-active molecules, candidates for medicines and others into cells, followed by inspecting the function of the gene in the cells or the physiological activity of the physiologically-active molecule in them. At present, an electroporation method, a gene gun method, a liposome method, a cell fusion method, a virus vector method and others are employed for transferring selected molecules, but, in any of these, selected molecules could not always be satisfactorily transferred into cells.

The electroporation method and the gene gun method may apply to many cells, but they require complicated operations and are difficult to modify for HTS (high throughput screening). The liposome method is problematic in that the cells to which it may apply are limited. In addition, these methods are all expensive, and even if they could be modified for HTS, they shall be extremely expensive. Further, most of them are not satisfactory in point of the transfer efficiency.

The human and mouse gene arrangements have now been clarified, and it is urgently necessary to analyze the genes having unknown functions so as to clarify their functions. In that situation, it is indispensable to develop a gene transfer method enough for HTS. Even in HTS, it is still desired that the method is efficient and enables functional analysis of various genes. For this, it is also urgently necessary to develop a high-efficiency gene transfer method not for specific limited cells but for various cells.

An object of the present invention is to solve the problems with the related art as above and to provide a high-efficiency method of transferring selected molecules into various types of cells and a method of fusing cells.

DISCLOSURE OF THE INVENTION

We, the present inventors have found that, when a cell and/or a selected molecule is/are processed with cold gas plasma, then the selected molecule existing around the cell is transferred into the cell, and have completed the present invention. Further, we have found that, when cell is processed with cold gas plasma, then they are fused.

Specifically, the invention is as follows:

[1] A method of transferring a selected molecule into a cell, which comprises processing a cell and/or a selected molecule with cold gas plasma to thereby transfer the selected molecule existing around the cell into the cell.

[2] The selected molecule transfer method of [1], wherein the selected molecule is previously made to exist around the cell, and the cell is then processed with cold plasma.

[3] The selected molecule transfer method of [1] or [2] wherein the selected molecule is polynucleotide.

[4] A method of fusing cells, which comprises processing cells with plasma.

[5] An apparatus for processing a target, which is a cell and/or selected molecule, with cold gas plasma to thereby transfer the selected molecule existing around the cell into the cell, or for processing cells with plasma to thereby fuse the cells.

[6] The apparatus in [5] for transferring a selected molecule is equipped with cold gas plasma generation unit comprising open-air discharge generate the cold gas plasma The selected molecules as referred to herein are molecules that are selected so as to be transferred into the intended cells. The selected molecules include high-molecular compounds, low-molecular physiologically-active substances, and candidates for medicines, for example, polynucleotides such as DNA, RNA and their derivatives, and proteins such as signal transfer proteins, transcriptional control factors and their derivatives. Of those selected molecules, preferred are polynucleotides and their derivatives.

The cells as referred to herein are the intended cells into which the selected molecules are transferred, and they are not specifically defined. Examples of the cells are procaryotic cells such as *Escherichia coli*, actinomycetes, *Bacillus subtilis*; and eucaryotic cells such as yeast, animal cells and vegetable cells. In addition, those having a lipid bilayer structure such as erythrocyte ghosts and liposomes are also within the scope of the cells in the invention.

For increasing the transfer efficiency of selected molecules into these cells, it is possible to use cells that are formed in accordance with an ordinary method of forming competent cells for gene transfer thereinto. If desired, the method of the invention may be combined with any other gene transfer method such as a liposome method of using cationic lipid, e.g., lipofectamin (GIBCO-BRL) or liposome, whereby the efficiency of the method of transferring selected molecules into the cells may be further increased.

The cold gas plasma (cold non-equilibrium plasma, cold weakly-ionized plasma) for use in the invention may be generated, for example, through corona discharging, and its properties may be varied depending on the type and the condition of the generation unit for it. Regarding the plasma that is used for carrying out the invention, the type of the gas for it, the plasma density, the electron temperature and the processing time with it may be suitably determined depending on the cells to be used and the selected molecules and also on the environment in which the operation is effected. Regarding the type of the gas to be used for the cold gas plasma, at least one selected from a group consisting of oxygen, air, carbon dioxide, nitrogen and argon is preferred.

The cold gas plasma generation unit to be used in the invention may be an open or closed unit. In view of the easiness with it in processing cells, preferred is an open unit.

Figure 1:
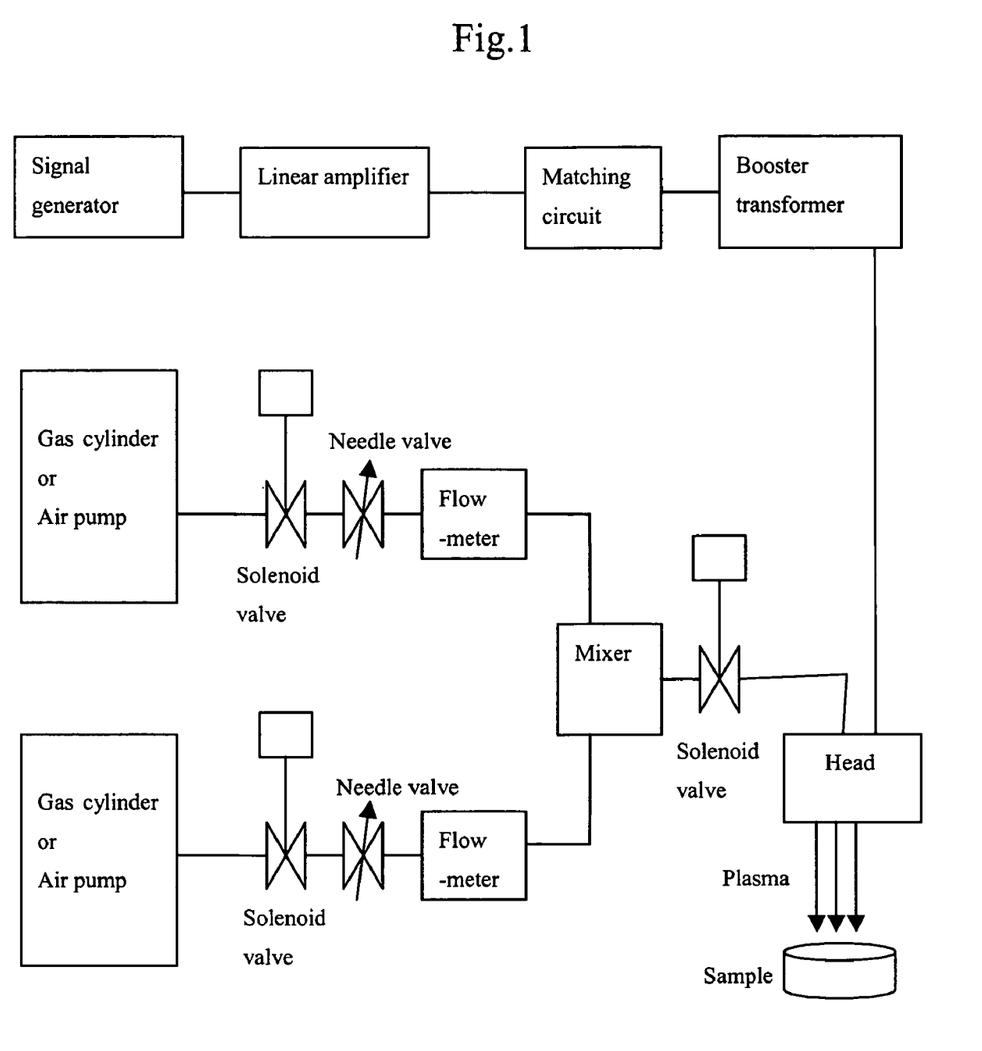
FIG. 1 is a schematic view showing an apparatus for gene transfer or cell fusion in the invention.
Figure 2:
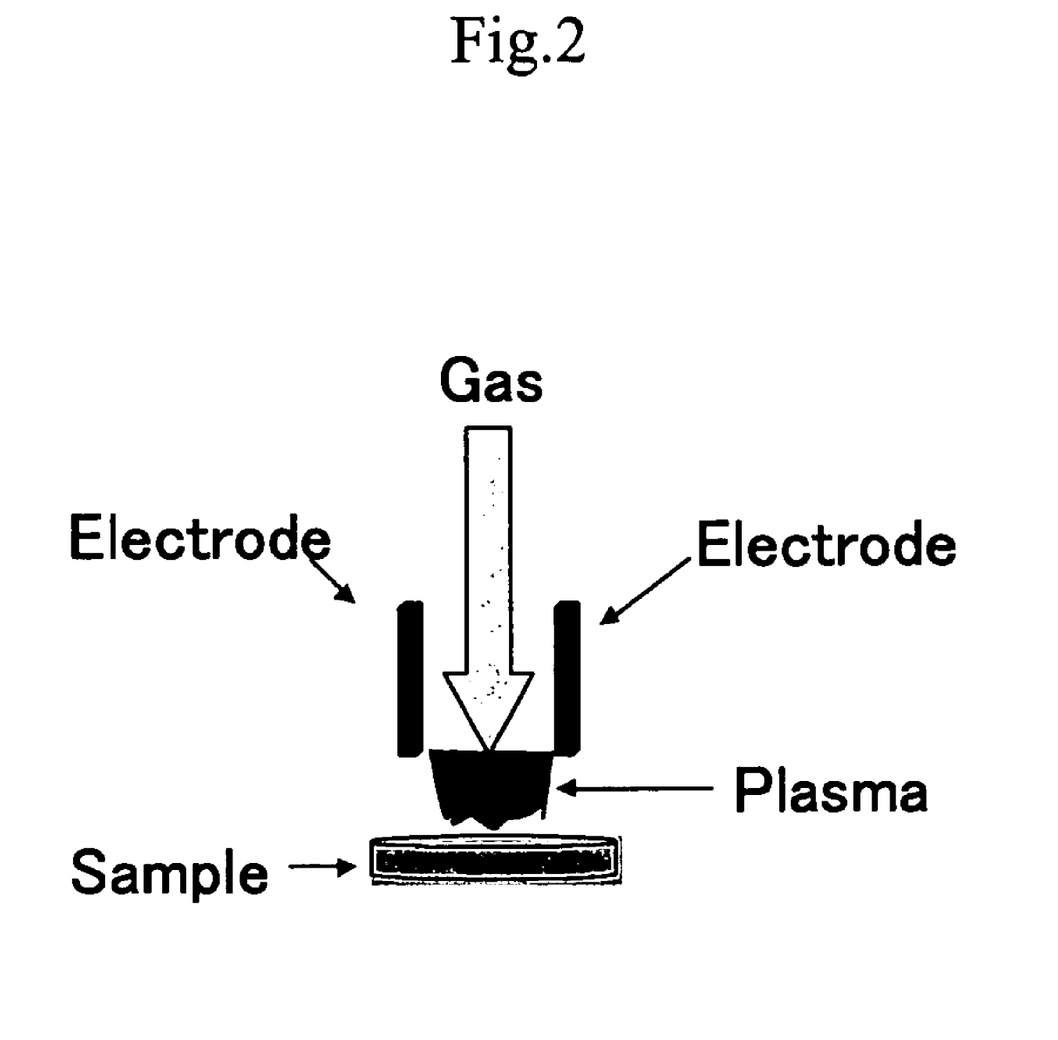
FIG. 2 is a schematic view showing the relationship between the plasma generator unit (electrode part) in the apparatus for gene transfer or cell fusion in the invention, and the sample to be processed with the unit.

A specific example of the apparatus of the invention is shown in FIG. 1. This apparatus comprises an electric line and a gas line. The electric line comprises a signal generator, a linear amplifier, a matching circuit and a booster transformer, and these act to control the parameters of inter-electrode voltage, inter-electrode distance, frequency, pulse period, duty and others. Under the controlled condition, the head is discharged to generate various plasmas. On the other hand, in the gas line, a single or mixed gas fed from a gas cylinder or an air pump passes through a needle valve to have a suitably-controlled flow rate, and fed to the head. The plasma having been generated in the head is blown out by the gas toward the sample that is set in front of the head. In order that the plasma irradiation may be effected in suitable conditions for every sample of cells, different types of organisms or selected molecules (including genes, low-molecular substances, proteins and others), these conditions may be varied to change the determination of the conditions for the plasma and its irradiation.

One specific embodiment of the invention comprises removing the culture from the cultured adhesive cells that have been cultured on a cell culture kit such as a plate, or from the cells that have been collected through centrifugation, filtration or the like, followed by adding a small amount of a solution of a selected molecule to the surface of each cell. Next, this is processed with plasma that has been generated by a plasma generator. The plasma processing time may fall generally between a few seconds and tens seconds, through varying depending on the plasma condition. After the plasma treatment, a medium is added to the cells and the cells are further cultured therein. In case where the selected molecule is a vector that contains a gene or the like, this is effective for gene recombination experiments. In case where the selected molecule is a candidate substance for a medicine that is targeted to a specific molecule in cells, this is effective for screening the candidates.

BEST MODES OF CARRYING OUT THE INVENTION

The invention is described more concretely with reference to the following Examples, to which, however, the invention should not be limited.

EXAMPLE 1

As in FIG. 1, an apparatus of the invention was constructed. The condition of the plasma generator in this apparatus is as follows: The inter-electrode voltage is from a few kV to more than ten kV; the inter-electrode distance is from 10 to 15 mm; the frequency is from 20 to 40 kHz; the pulse period is from 30 to 90 Hz; the duty is from 25 to 100%; the gas is any of air, nitrogen, oxygen, carbon dioxide, argon, or helium/air=1/1, and its irradiation time is approximately from 1 to 5 seconds. The distance between the electrode and the sample is approximately from 1 to 3 cm. Within the range, a suitable condition for the sample was selected.

Figure 3:
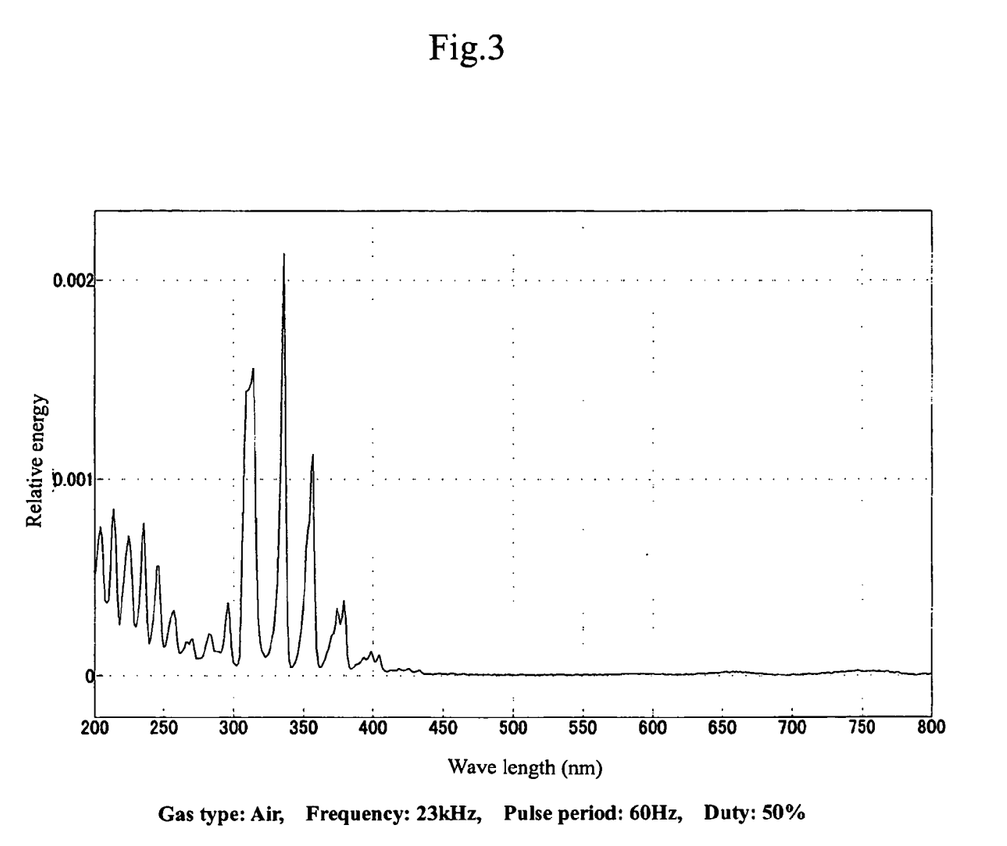
FIG. 3, FIG. 4 and FIG. 5 each show the spectral data of the plasma having been generated under different conditions in the apparatus used for gene transfer or cell fusion in the Examples of the invention. For measuring the data, a spectrophotometer, Otsuka Electronics' MCPD-3000 was used. Separated by about 3 cm from the plasma, a probe was set to receive the spectrum of the plasma.
Figure 4:
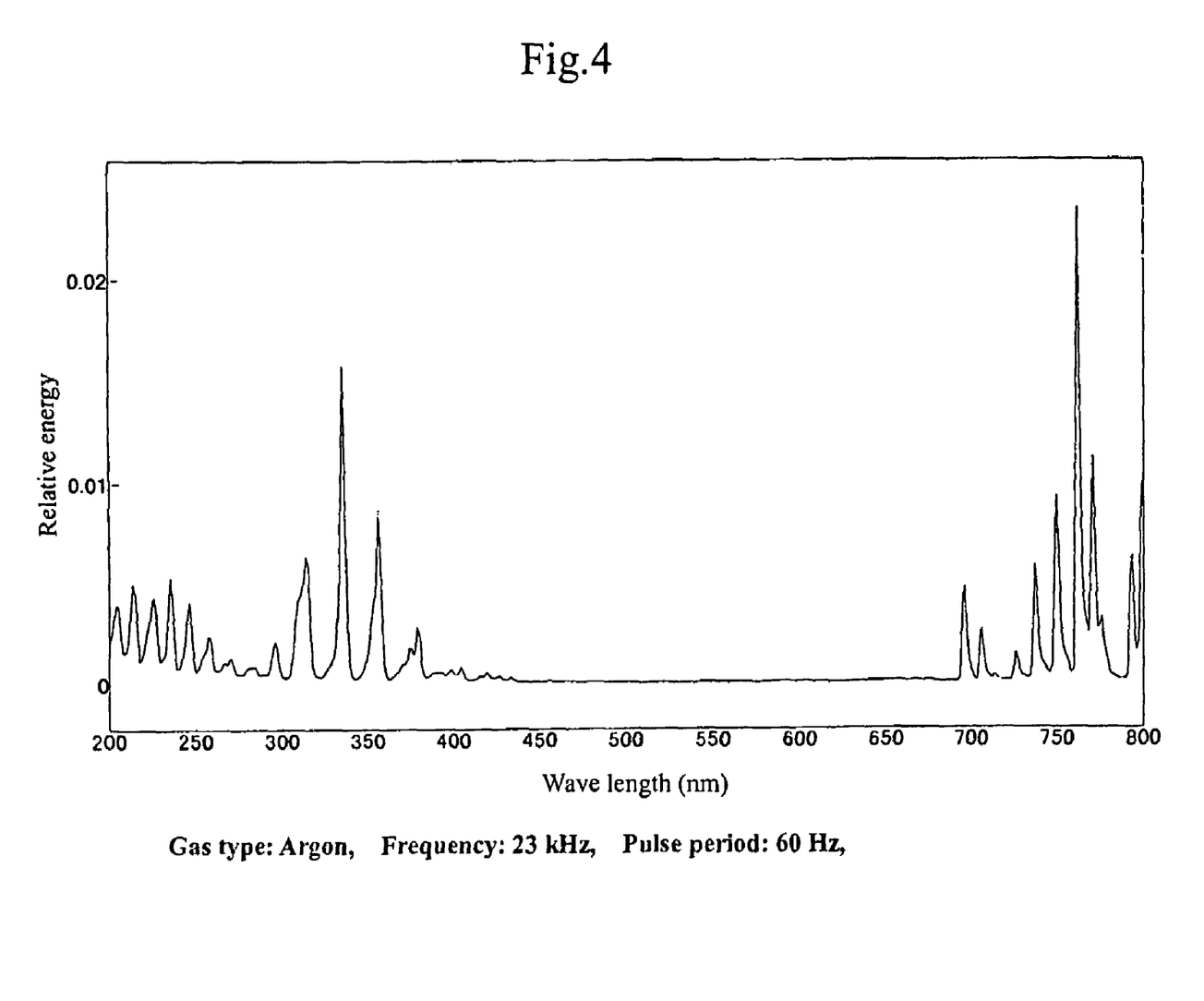
Figure 5:
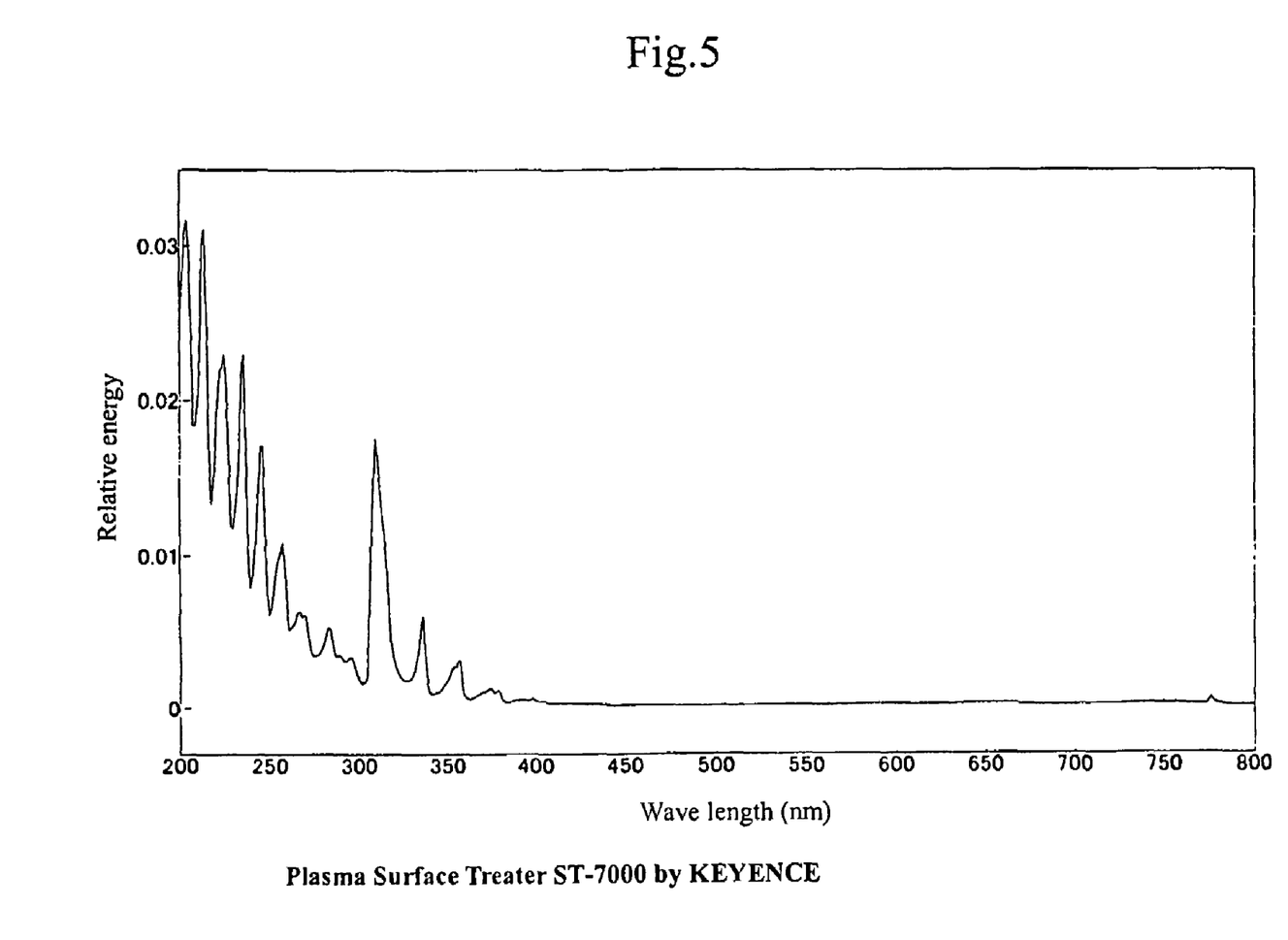

In this apparatus, for example, plasma having the spectrum as in FIG. 3 to FIG. 5 can be generated. Using the plasma generation apparatus, gene transfer was carried out herein.

Chinese hamster pulmonary fibroblasts, CHL cells were sowed in a cell culture plate having a diameter of 60 mm, and cultured overnight at 37° C. under the condition of 5% carbon dioxide. The number of the cells first sowed at the start of the culture was $1\times10^6$ cells/well. After it was confirmed that the cells well adhered to the plate, the medium was removed from the culture plate, and 110 µl of a GFP expression plasmid liquid (1 µg/µl) was added to the cell surface. Then, this was subjected to plasma irradiation under various conditions with the apparatus of the invention. Immediately after the plasma irradiation, a medium was added thereto and the cells were cultured overnight. Then, the cells were observed with a fluorescence microscope for expression of GFP protein, and the number of the expressing cells per the field of view was counted. In addition, the GFP protein-expressing cells per all the cells in every well were quantified through FACS flow cytometry.

As a result, GFP expression was observed under every condition. The transfer efficiency was at most about 60% in microscopic observation and was approximately from 5 to 25% in FACS inspection.

A plasma generator, Plasma Surface Treater ST-7000, sold on the market by KEYENCE is an apparatus of the same type as that of the apparatus used herein. This may generate plasma having the spectrum as in FIG. 5, and this may be usable for the object of the invention.

EXAMPLE 2

2-1) Transfer into adhesive cells of established animal cell line

Established animal cells were sowed in a 6-well plate and cultured overnight at 37° C. under the condition of 5% carbon dioxide. The number of the cells, Chinese hamster fibroblasts CHL cells first sowed at the start of the culture was $1\times10^6$ cells/well; and that of human uterine cancer-derived Hela cells was $2.5\times10^5$ cells/well. After it was confirmed that the cells well adhered to the plate, the medium was removed from the culture plate, and 50 µl of a GFP expression plasmid (pEGFP-C1) liquid (1 µg/µl) was added to the cell surface. Then, this was subjected to plasma irradiation with a plasma generator. The condition of the plasma generator was as follows: The inter-electrode voltage during discharge was from 10 to 14 kV; the inter-electrode distance was 13 mm; the frequency was 23.3 kHz; the pulse period was 60 Hz; the duty was 50%; and the gas, air flow rate was 38 liters/min. The irradiation was effected for about 3 seconds. The distance between the electrode and the sample was suitably determined. Immediately after the plasma irradiation, a medium was added thereto and the cells were cultured overnight. Then, the cells were observed with a fluorescence microscope for expression of GFP protein, and the number of the expressing cells per the field of view was counted. In addition, the GFP protein-expressing cells per all the cells in every well were quantified through FACS flow cytometry.

As a result, GFP expression was observed in all types of the cells. Under the condition that the inter-electrode voltage during discharge was from 10 to 14 kV, the inter-electrode distance was 13 mm, the frequency was 20 kHz; the pulse period was 60 Hz; the duty was 50%; and the gas, air flow rate was 38 liters/min, the transfer efficiency was at most about 70% in microscopic observation and was about 30% in FACS inspection (this is the gene transfer efficiency per the number of all the cells in the dish). It is said that the transfer efficiency with Hela cells is low in existing methods, but the method of the invention has made it possible to attain a high transfer efficiency of about 70% or so in some region.

EXAMPLE 3

Transfer into planktonic cells of established animal cell line

A phosphate buffer suspension of human acute lymphoblastic leukemic peripheral blood-derived T cell-line Jurkat cells, 2.25 ×10$^7$ cells/ml, was prepared. 25 µl of the cell suspension was mixed with the same amount of a GFP expression plasmid solution (2 µg/µl), and the resulting mixture was put into a fresh 6-well plate. Its amount was 50 µl/well. This was spread thin in the bottom of each well, and then irradiated with plasma with a plasma generator. In this Example, the plasma generator was driven as in Example 1. Immediately after the plasma irradiation, a medium was added thereto and the cells were cultured overnight at 37° C. under the condition of 5% carbon dioxide. Then, the cells were observed with a fluorescence microscope for expression of GFP protein. In addition, the GFP protein-expressing cells per all the cells in every well were quantified through FACS flow cytometry.

As a result, GFP protein expression was confirmed in observation with a fluorescence microscope. The transfer efficiency confirmed through FACS was about 25%.

EXAMPLE 4

Transfer into rat cerebral cortex cells

A rat cerebral cortex was prepared as follows: A pregnant rat (Wister, 17-day pregnant) was anesthetized and its uterus with its fetus therein was taken out through abdominal operation into L-15 (GIBCO-BRL). Then, the cerebral cortex site was separated from the whole brain of the fetus. 40 ml of 0.25% trypsin solution and 80 µl of 1% DNAse solution were added to the cerebral cortex site, which was then incubated at 37° C. for 20 minutes. The resulting supernatant was removed, and 10 ml of FBS was added to the residue. This was pipetted to loosen the cells. This was passed through a cell strainer, and about 20 ml of a Neurobasal medium (GIBCO-BRL) was added thereto, and the cells were collected through centrifugation. The cells were suspended in a Neurobasal medium for culture initiation (25 µM glutamic acid, 500 µM glutamine, 30 nM NaSeO$_3$, containing penicillin and streptomycin) to be 5×10$^5$ cells/ml, and these were cultured in a 6-well plate at 37° C. under the condition of 5% carbon dioxide.

After it was confirmed that the cells well adhered to the plate, the medium was removed from the culture plate, and 50 µl of a GFP expression plasmid liquid (1 µg/µl) was added to the cell surface. Then, this was subjected to plasma irradiation with a plasma generator. The condition of the plasma generator was as follows: The inter-electrode voltage during discharge was from 10 to 14 kV; the inter-electrode distance was 13 mm; the frequency was 23.3 kHz; the pulse period was 60 Hz; the duty was 50%; and the gas, air flow rate was 38 liters/min. The irradiation was effected for about 1 second. Immediately after the plasma irradiation, a medium was added thereto and the cells were cultured overnight. Then, the cells were observed with a fluorescence microscope for expression of GFP protein.

As a result, GFP protein-expressing cells were found. The transfer efficiency was at most about 70% per field of view. Gene transfer into the primary-cultured animal cells as herein was almost impossible in existing gene-transfer methods. The method of the present invention has enabled safe, simple and efficient gene transfer into the primary-cultured animal cells.

EXAMPLE 5

Transfer into rat cerebellar granular cells

A 9-day-old Wister rat was anesthetized with ether and its brain was taken out. The cerebellum was cut out of it, and its meninx was removed. The cerebellum was cut into pieces, and 10 ml of a papain solution (this was prepared by mixing 90 units of papain (Worthington-biochem) in 10 ml of a phosphate buffer with 2 mg of DL-cysteine (Sigma) and 50 mg of albumin dissolved therein, leaving the resulting mixture at 37° C. for a while to activate it, then adding thereto 50 µl of DNase I (Takara), and before use, this was filtered and sterilized) was added thereto, and shaken at 37° C. for about 30 minutes. 6 ml of horse serum (HS) was added to it and centrifuged. The resulting tissue deposit was suspended in a serum medium (5% PFCS and 5% HS containing DME/F12 (1/1) medium). This was sowed in a polyethylenimine-coated 6-well plate to be 2.5×10$^6$ cells/well, and cultured overnight at 37° C. under the condition of 5% carbon dioxide. With that, the medium was exchanged with a high-potassium (26 mM), 1 µM AraC (Sigma)—containing medium (5% HS, potassium bicarbonate/2.1 g, 30 nMNa$_2$SeO$_4$in MEM (Sigma)), and the cells were further cultured for 5 days at 37° C. under the condition of 5% carbon dioxide.

After it was confirmed that the cells well adhered to the plate, the medium was removed from the culture plate, and 50 µl of a GFP expression plasmid liquid (1 µg/µl) was added to the cell surface. Then, this was subjected to plasma irradiation with a plasma generator. The condition of the plasma generator was as follows: The inter-electrode voltage during discharge was from 10 to 14 kV; the inter-electrode distance was 13 mm; the frequency was 23.3 kHz; the pulse period was 60 Hz; the duty was 50%; and the gas, air flow rate was 38 liters/min. The irradiation was effected for about 1 second. Immediately after the plasma irradiation, a medium was added thereto and the cells were cultured overnight. Then, the cells were observed with a fluorescence microscope for expression of GFP protein.

As a result, GFP protein-expressing cells were found. The transfer efficiency was at most about 40% per field of view. Gene transfer into the primary-cultured animal cells as herein was almost impossible in existing gene-transfer methods. The method of the present invention has enabled safe, simple and efficient gene transfer into the primary-cultured animal cells.

EXAMPLE 6

Transfer into human umbilical vein-derived hemal endothelial cells (HUVEC)

Cells were cultured, using Total Kit (Toyobo) for normal human umbilical vein endothelial cells.

Normal human umbilical vein endothelial cells (HUVEC) were sowed in a 6-well plate to be 2.5×10$^5$ cells/well, and cultured overnight at 37° C. under the condition of 5% carbon dioxide. After it was confirmed that the cells well adhered to the plate, the medium was removed from the culture plate, and 50 µl of a GFP expression plasmid liquid (1 µg/µl) was added to the cell surface. Then, this was subjected to plasma irradiation with a plasma generator. The condition of the plasma generator was as follows: The inter-electrode voltage during discharge was from 10 to 14 kV; the inter-electrode distance was 13 mm; the frequency was 23.3 kHz; the pulse period was 60 Hz; the duty was 50%; and the gas, air flow rate was 38 liters/min. The irradiation was effected for about 1 second or 3 seconds. Immediately after the plasma irradiation, a medium was added thereto and the cells were cultured overnight. Then, the cells were observed with a fluorescence microscope for expression of GFP protein.

As a result, GFP gene transfer was confirmed also into the human umbilical vein-derived hemal endothelial cells. The transfer efficiency was at most about 50% per field of view. Gene transfer into the primary-cultured animal cells as herein was almost impossible in existing gene-transfer methods. The method of the present invention has enabled safe, simple and efficient gene transfer into the primary-cultured animal cells.

EXAMPLE 7

Differentiation induction of PC12 cells into sympathetic nervous system

This is to investigate as to whether or not the cells processed according to the method of the invention for gene transfer thereinto could still maintain their function. Concretely, PC12 cells were tested for differentiation potency into sympathetic nervous systems.

A GFP gene was transferred into PC12 cells according to the method of the invention as in Example 1. NGF was added to the culture of the cells to be 100 ng/ml, and the cells were cultured for 6 days. Then, the morphology of the PC12 cells that had been confirmed to have expressed GFP protein with a fluorescence microscope was observed to check them for differentiation potency into sympathetic cells.

As a result, the PC12 cells having the GFP gene transferred thereinto according to the method of the invention still expressed GFP protein even in 6 days after the NGF addition thereto, and in addition, the cell morphology observation surely supported neural process extension from the cells. This confirms that the gene transfer method assisted by plasma irradiation does not change the property intrinsic to PC12 cells for differentiation potency with NGF into sympathetic cells.

EXAMPLE 8

CREB activation through gene transfer into PC12 cells (reporter gene assay)

This is to investigate as to whether or not the gene having been transferred into cells according to the method of the invention could exhibit its function in the cells. Concretely, PC12 cells with CREB and PKA transferred thereinto were analyzed through reporter gene assay as to whether or not CREB therein could be activated by the PKA gene also therein.

Rat pheochromocytoma PC12 cells (ATCC No. CRL-1721) were sowed in a collagen IV-coated 6-well plate to be $1 \times 10^6$ cells/well, and cultured overnight at 37° C. under the condition of 5% carbon dioxide. After it was confirmed that the cells well adhered to the plate, the medium was removed from the culture plate. Then, the cells were processed with a mixture that had been prepared by mixing a PKA gene (pFC-PKA) (1 µg/µl), a CREB reporter gene (pCRE-Luc) with a luciferase gene linked downstream the response sequence of activated CREB (1 µg/µl) and an internal standard, *Renilla* luciferase gene (pRL-SV40) of 17 µl each, according to the method of the invention as in Example 2 to thereby co-transfer the genes into the PC12 cells. One day after the gene transfer, the PC12 cells were checked for luciferase activity.

As a result, significant luciferase activity increase, or that is, significant CREB transcription activity increase was found in the PKA-transferred cells as compared with the control vector-transferred cells. This confirms that the gene having been transferred into PC12 cells of an established culture cell line according to the gene transfer method associated with plasma irradiation exhibits its function in the cells.

EXAMPLE 9

CREB activation through gene transfer into rat cerebellar granular cells (reporter gene assay)

This is to investigate as to whether or not the same result as above could be obtained even in primary-cultured animal cells into which gene transfer is difficult according to conventional methods. For this, rat cerebellar granular cells were tried in the same manner as in Example 8.

Rat cerebellar granular cells were established in the same manner as in Example 5. A PKA gene (pFC-PKA) (1 µg/µl), a CREB reporter gene (pCRE-Luc) with a luciferase gene linked downstream the response sequence of activated CREB (1 µg/µl) and an internal standard, *Renilla* luciferase gene (pRL-SV40) were co-transferred into the cells by the use of a plasma generator as in Example 2, and the cells were then cultured for 1 day. Then, the cells were checked for luciferase activity.

As a result, the luciferase activity of the primary rat neurocytes significantly increased as compared with the control gene-transferred cells. Accordingly, this confirms that, even in primary rat neurocytes (rat cerebellar granular cells), the plasma transfer method gives no abnormality to the CREB signal transfer pathway by PKA.

From the above, it has been clarified that the gene transfer method associated with plasma irradiation makes it possible to transfer a gene even into primary neurocytes, into which gene transfer is difficult in conventional methods, and the transferred gene can express its function in the cells, and that the method simplifies reporter gene assay.

EXAMPLE 10

Apoptosis induction through BAD gene transfer into rat cerebellar granular cells Rat cerebellar granular cells were prepared in the same manner as in Example 5. 5 days after AraC addition thereto, the medium was removed from the cells. A solution of an apoptosis-inducing gene, BAD gene (pcDNA3.1/GS-BAD) (1 µg/50 µl) was added to the cells to be 50 µl/well, and the cells were subjected to plasma irradiation under the same condition as in Example 2. Immediately after this, a medium was added thereto, and the cells were cultured overnight at 37° C. under the condition of 5% carbon dioxide. With that, the caspase activity of the cells was measured with CaspASE FITC-VAD-FMK in-situ Marker (Promega) to investigate as to whether or not apoptosis was induced in the cells.

As a result, a significant caspase activity was found in the BAD gene-transferred cells, as compared with the MOCK cells into which the vector alone was transferred. Namely, apoptosis-induced cells were detected.

In addition, the cells were further checked for DNA fragmentation by the use of APO-DIRECT (Pharmingen) for the purpose of confirming as to whether the cells, into which the BAD gene had been transferred according to the method of the invention, were surely induced to apoptosis.

As a result, cells with significant DNA fragmentation were detected in the BAD gene-transferred cells as compared with the MOCK cells with the vector alone transferred thereinto.

The result confirms that the BAD gene having been transferred into rat cerebellar granular cells according to the method of the invention significantly induced apoptosis in the cells and exhibited its function. From the above, it has been confirmed that the gene transferred into primary culture cells according to the method of the invention surely exhibits its function in the cells.

EXAMPLE 11

Investigation of cell fusion with Chinese hamster lung-derived CHL cells, human uterus cancer-derived Hela cells, and rat pheochromocytoma PC12 cells In the same manner as in Example 2, a GFP gene was transferred into CHL cells and into Hela cells. These cells were checked for fused cells, using a fluorescence microscope. The cells were stained with Dif Quick (International Reagents) on their nuclei, and the situation of the fused cells was observed with a microscope. The nuclei were stained as follows: After processed with plasma, the cells were cultured for one day, and the culture liquid was absorbed away from the cells. Then, the cells having adhered to the dish were washed with a phosphate buffer, and about 5 ml/well of methanol (Wako) was added thereto, and the cells were fixed for 5 minutes at room temperature. About 2 ml/well of staining liquid I was added to them, and this was immediately absorbed away. Next, about 2 ml/well of staining liquid II was added thereto, and this was also immediately absorbed away. The adhesive cells were washed a few times with ion-exchanged water, and then observed with a microscope.

In the CHL and Hela cells with a GFP gene transferred thereinto according to the method of the invention, fused large cells were found. When the nucleus of each cell processed through plasma irradiation was stained, it was found that some cells were fused along with their nuclei and some others were fused to give polynuclear cells.

On the other hand, a GFP gene was transferred into rat pheochromocytoma PC12 cells in the same manner as in Example 1, for which, however, the number of the cells sowed in the 6-well plate was $5 \times 10^6$/well and was relatively large. NGF was added to the cells in the same manner as in Example 7, and the cells were checked for differentiation potency.

Even the fused cells expressed GFP protein in 6 days after the NGF addition, and neural process extension was surely found from the fused cells. This suggests that the fused cells formed through plasma irradiation also do not change the property intrinsic to PC12 cells for differentiation potency with NGF into sympathetic cells.

EXAMPLE 12

Combination with liposome method

This is to investigate as to whether or not the method of the invention enables gene transfer into cells even under difficult conditions for liposome-assisted gene transfer.

In the liposome method, a liposome reagent and a transfer plasmid are mixed to prepare mixed particles having a suitable size, and the particles are introduced into cells. Accordingly, in the method, a predetermined number of particles having a predetermined size must be prepared. This Example is to investigate as to whether or not the gene transfer efficiency could be improved under more difficult conditions having a higher plasmid concentration and a higher liposome reagent condition than in the optimized conditions. In this, a GFP gene was transferred into cells.

Concretely, 100 μg of a GFP expression plasmid and 100 μl of Lipofectin 2000 (GIBCO-BRL) were previously mixed and left at room temperature for 15 minutes to prepare a plasmid/Lipofectin conjugate. From the previously day, CHL cells were kept cultured in a 6-well plate, and the culture supernatant was removed from the plate. With that, 200 μl of the plasmid/Lipofectin conjugate was added to the plate. Using a plasma generator, this was irradiated with plasma. The condition was as follows: The frequency was 23.3 kHz, the pulse period was 60 Hz, the duty was 50%, and the gas, air flow rate was 38 liters/min. Immediately after the plasma irradiation, a medium was added thereto, and the cells were cultured at 37° C. under the condition of 5% carbon dioxide. After cultured for one day, the cells were observed with a fluorescence microscope, and the GFP protein-expressing cells were detected through FACS.

Even in this condition, a few cells were found to have GFP transferred thereinto in a liposome method alone. In the combination with the method of the invention, the gene-transferred cells in the plasma irradiation range increased as compared with the liposome method alone. In addition, the ratio of the gene-transferred cells to all the cells in each well was obtained through FACS. It was found that the transfer efficiency in the combination with the method of the invention increased by about 1.6 times as compared with the liposome method alone. Accordingly, when the method of the invention is combined with any other gene transfer method, or when a liposome or any other carrier substitutable with it and capable of promoting plasmid transfer into cells is bound for use in the method of the invention, the transfer efficiency could be improved even in difficult cells and under difficult conditions in and under which the transfer efficiency has heretofore been not good.

EXAMPLE 13

In this, a plasma generator was tested for GFP-expression plasmid transfer into cultured cells.

The method is as follows: Rat pheochromocytoma PC12 cells (ATCC No. CRL-1721) were sowed in a collagen IV-coated 6-well plate to be $1 \times 10^6$ cells/well, and cultured overnight. After it was confirmed that the cells well adhered to the plate, the medium was removed from the culture plate, and 50 μl of a GFP expression plasmid liquid (1 μg/μl) was added to the cell surface. Then, this was subjected to plasma irradiation with a plasma generator, Plasma Suface Treater ST-7000 (by KEYENCE). Regarding the condition for the plasma generator ST-7000, the frequency was any of three conditions of high, low or metal, and the irradiation continued for about 5 seconds in every case. Immediately after the plasma irradiation, a medium was added thereto and the cells were cultured overnight. Using a fluorescence microscope, the cells were checked for expression of GFP protein therein.

The result is as follows: In every condition, GFP expression was found in the cells.

The transfer efficiency was the highest in the high frequency condition, falling between 50 and 60%.

EXAMPLE 14

Evans blue (10 mg/ml physiological saline) was thinly applied to all over the abdomen of a nude mouse (8 weeks-old, female, Nippon Charles River) in anesthetization. Using a plasma generator, this was irradiated with plasma. The inter-electrode voltage during discharge was from 10 to 14 kV; the inter-electrode distance was 13 mm; the frequency was 23.3 kHz; the pulse period was 60 Hz; the duty was 50%; and the gas, air flow rate was 38 liters/min. The irradiation was effected for 2.5 seconds. The distance between the electrode and the abdomen was from about 24 mm in the remotest to about 18 mm in the nearest. This was left as such for about 3 minutes, and then the Evans blue-applied site was fully wiped with absorbent cotton wetted with water and then absorbent cotton wetted with 70% ethanol. With that, the skin was checked for dye deposition. Thus processed, the mouse was compared with another subjected to plasma irradiation alone and with still another coated with Evans blue but not subjected to plasma irradiation.

As a result, no dye deposition was found in both the mouse subjected to plasma irradiation alone and the mouse coated with Evans blue but not subjected to plasma irradiation. As opposed to these, the mouse coated with Evans blue and subjected to plasma irradiation had some blue spots in the plasma-irradiated region of the abdomen thereof. Even after about 24 hours, the spots were still seen. Accordingly, it is believed that substances of which the molecular weight is on the level of Evans blue could be transferred into animal individuals through plasma irradiation.

Heretofore, a report has been announced, saying that dye is percutaneously transferred into animal individuals through irradiation with cold ultrasonic waves (Katsuro Tachibana; the Medical Department of Fukuoka University/the Society of Molecular Biology of Japan, 2001). The present invention suggests that substance transfer into animal individuals is also possible through plasma irradiation.

INDUSTRIAL APPLICABILITY

The present invention has enabled high-efficiency transfer of a variety of selected molecules into a variety of cells. It has enabled cell fusion as well. In addition, the invention does not require any complicated operation of applying an electric field to every one sample by the use of electrodes as in electroporation, and does not require any large-scale apparatus such as gene guns.

The invention claimed is:

1. A method for transferring a selected molecule into a cell, which comprises:
    contacting a mammalian cell with a solution comprising the selected molecule;
    generating a cold gas plasma;
    applying said cold gas plasma to said cell and solution of the selected molecule such that the selected molecule transfers into the cell.

2. The method as claimed in claim 1, wherein the selected molecule is a polynucleotide.

3. The method as claimed in claim 2, wherein the selected molecule is DNA.

4. The method as claimed in claim 2, wherein the selected molecule is RNA.

5. The method as claimed in claim 1, wherein the selected molecule is a protein.

6. The method as claimed in claim 1, wherein the gas used for cold gas plasma is air.

7. The method as claimed in claim 1, wherein the gas used for cold gas plasma is oxygen.

8. The method as claimed in claim 1, wherein the gas used for cold gas plasma is carbon dioxide.

9. The method as claimed in claim 1, wherein the gas used for cold gas plasma is argon.

10. The method as claimed in claim 1, further comprising culturing the cell after transfer of said selected molecule.

11. The method as claimed in claim 1, further comprising selecting a cell that has taken up the selected molecule and culturing said cell.

* * * * *